United States Patent [19]

Suarato et al.

[11] 4,188,377

[45] Feb. 12, 1980

[54] CARMINOMYCIN DERIVATIVES, THEIR PREPARATION AND USE

[75] Inventors: Antonino Suarato; Paolo Masi; Luigi Bernardi; Federico Arcamone, all of Milan, Italy

[73] Assignee: Farmitalia Carlo Erba S.p.A., Milan, Italy

[21] Appl. No.: 872,626

[22] Filed: Jan. 26, 1978

[30] Foreign Application Priority Data

Feb. 1, 1977 [GB] United Kingdom ............... 04104/77

[51] Int. Cl.$^2$ ....................... A61K 31/70; C07H 15/24
[52] U.S. Cl. .................................. 424/180; 536/17 A
[58] Field of Search ................ 536/17, 17 A; 424/180

[56] References Cited

U.S. PATENT DOCUMENTS 4,035,566  7/1977  Israel et al. ..................... 536/17 A

OTHER PUBLICATIONS

Kendo, et al. "Jour. Amer. Chem. Soc.", vol. 98, Mar. 31, 1976, pp. 1967-1969.

Primary Examiner—Johnnie R. Brown
Attorney, Agent, or Firm—Hubbell, Cohen, Stiefel & Gross

[57] ABSTRACT

N-acyl derivatives of the known antitumor antibiotic carminomycin, particularly N-trifluoroacetyl carminomycin, have a much lower toxicity than carminomycin.

4 Claims, No Drawings

CARMINOMYCIN DERIVATIVES, THEIR PREPARATION AND USE

BACKGROUND OF THE INVENTION

1. Field of the Invention

The invention relates to antitumor anthracycline antibiotics and more particularly, to N-acyl derivatives of the known antitumor antibiotic carminomycin.

2. The Prior Art

It is well known that carminomycin is a natural anthracycline antibiotic which displays antitumor activity in humans and animals (G. F. Gause, M. G. Brazhnikova and V. A. Shorin, Cancer Chemother. Rep., Part 1, 58, 255 (1974)). Unfortunately, the therapeutic usefulness of carminomycin is severely restricted because of its high toxicity. Moreover, carminomycin can be obtained in only limited amounts from natural sources and no practical syntheses for carminomycin are known; although a total synthesis of the aglycone has been reported in the literature (Kende et al, J. Am. Chem. Soc. 98, 1967 (1976)).

SUMMARY OF THE INVENTION

The present invention relates to carminomycin derivatives and to a synthetic process for the manufacture of carminomycin and its derivatives which are provided by the invention.

The present invention provides, in one aspect thereof, N-acyl derivatives of carminomycin of the formula I:

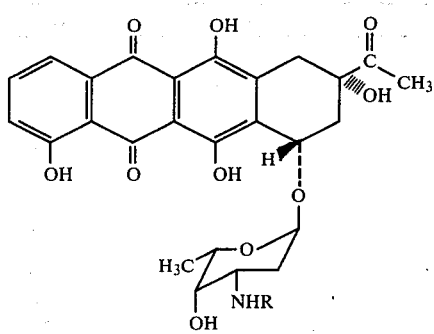

wherein R is an acyl group selected from the group consisting of acetyl, mono, di and trichloroacetyl, trifluoroacetyl, benzoyl and substituted benzoyl. Presently, the most preferred such compound is the trifluoroacetyl derivative.

According to the invention, the compounds of formula I [wherein R, in addition to being as defined above, may also be hydrogen—in which case, the compound is the known antibiotic carminomycin], are prepared from daunomycinone (II), according to scheme I (below), with particular emphasis on the new N-acyl derivatives of carminomycin. As shown in scheme I, daunomycinone (II) is demethylated with a Lewis acid such as aluminum trichloride, or tribromide, to form the aglycone of carminomycin (III). The latter is then condensed with a 2,3,6-trideoxy-3-acylamido-4-O-acyl-α-L-lyxopyranosyl chloride to yield compound (IV), wherein the acyl groups are R, as defined above.

A mild hydrolysis of (IV) in methanol containing triethylamine leads to the N-acyl derivatives of carminomycin (I; R=the acyl groups as specified above, preferably, trifluoroacetyl). When R is trifluoroacetyl, the compound (I) in turn can be transformed into carminomycin itself (I; R=H) by treatment with an aqueous alkaline base.

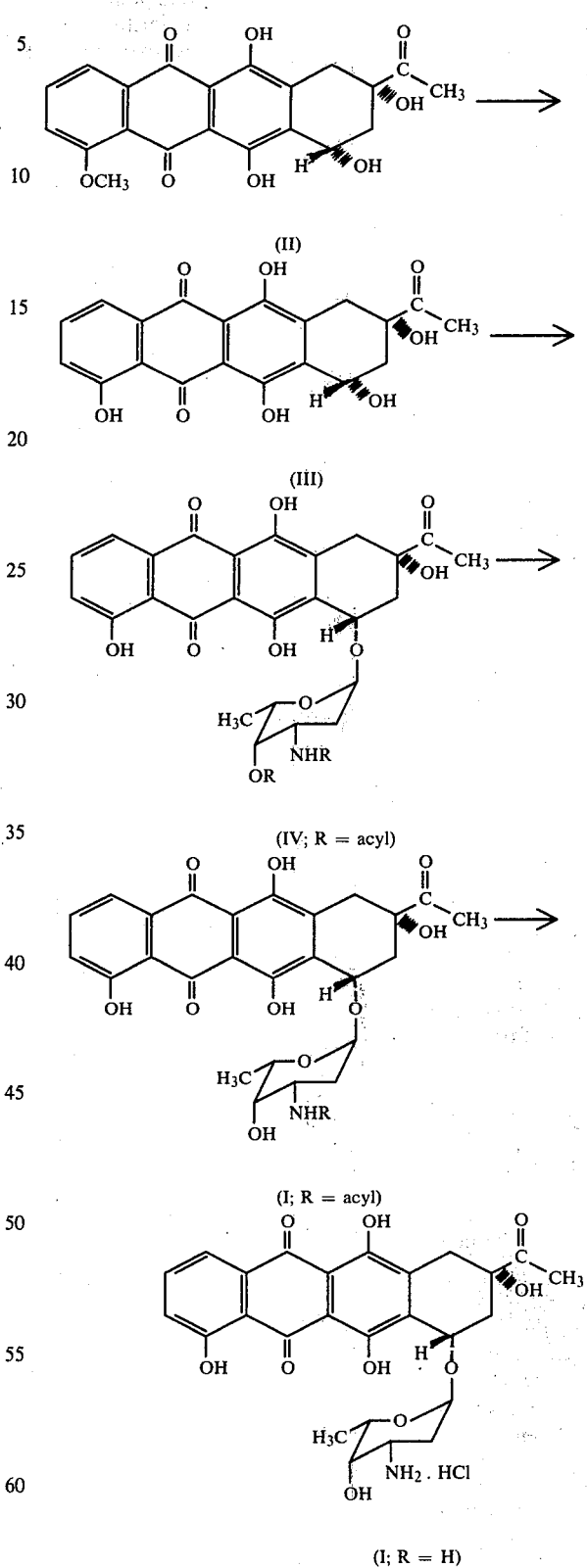

In yet another aspect, the invention provides a method of treating certain mammalian tumors using the new N-acyl derivatives of carminomycin. These new N-acyl derivatives of carminomycin are endowed with antitumor activity in mammals and are much less toxic than the parent compound, carminomycin.

In particular, N-trifluoroacetylcarminomycin, because of its very low toxicity, can be administered at very high doses which results in a more effective antitumor activity than carminomycin itself.

DESCRIPTION OF THE PREFERRED EMBODIMENTS

The following examples are given to more clearly describe the invention. Unless otherwise specified, all parts given are by weight.

EXAMPLE 1

4-Demethoxy-4-hydroxydaunomycinone (III)

To a refluxed solution of 10 g. of daunomycinone (II) in 1 liter of dichloromethane, 30 g. of aluminum trichloride were added over a two hour period with stirring. After an additional 4 hour period, the reaction mixture was cooled and poured into ice water containing 150 g. of oxalic acid. The organic layer was separated, washed with water and concentrated in vacuo to yield 6 g. of crystalline 4-demethoxy-4-hydroxy-daunomycinone (III), which were collected by filtration.

EXAMPLE 2

N-trifluoroacetylcarminomycin (I; R=CF$_3$CO—)

To a solution of 1 g. of 4-demethoxy-4-hydroxydaunomycinone (III) and 0.850 g. of 2,3,6-trideoxy-3-trifluoroacetamido-4-O-trifluoroacetyl-α-L-lyxopyranosyl chloride in a 1:1 mixture of dimethyl formamide and dichloromethane, a solution of 0.570 g. of silver trifluoromethanesulfonate in 15 ml. of anhydrous diethyl ether was added dropwise at room temperature. After 1 hour of stirring, the reaction mixture was diluted with dichloromethane, washed with an aqueous solution of NaHCO$_3$ and finally with water. The solvent was removed in vacuo and the residue taken up in chloroform. The insoluble starting material was removed by filtration, and the filtrate was evaporated to a residue which was then dissolved in methanol containing a trace of triethylamine. The resulting solution was left to stand for 2 hours at room temperature. Removal of the solvent in vacuo and purification of the residue by column chromatography (silica gel; chloroform/acetone 95:5, v/v) afforded 0.370 g. of N-trifluoroacetyl carminomycin I; R=CF$_3$CO—).

EXAMPLE 3

Carminomycin hydrochloride (I; R=H)

0.5 grams of N-trifluoroacetyl carminomycin (I; R=CF$_3$CO—) was dissolved in 0.15 N NaOH and left standing for 2 hours at room temperature. After acidification with oxalic acid and neutralization with aqueous NaHCO$_3$, the free base with extracted with dichloromethane which was washed with water. The solvent was removed in vacuo and the resulting residue was dissolved in dry dichloromethane and treated with 1 equivalent of HCl in methanol. The solution was then concentrated in vacuo and diethyl ether was added to precipitate 0.300 g. of carminomycin hydrochloride (I; R=H), which was found to be identical to an authentic sample.

Biological Activity

The activity of N-trifluoroacetyl carminomycin (I; R=CF$_3$CO—) on P$_{388}$ lymphocytic leukemia in CDF$_1$ male mice (tumor inoculum 10$^6$ cells i.p.) in comparison with daunorubicin, doxorubicin and carminomycin was determined. Treatment i.p. was effected on days 5, 9 and 13 after inoculation[a]

Table 1

|  | Dose mg./kg. | T/C[b] |
|---|---|---|
| Daunorubicin | 8 | 126 |
|  | 4 | 115 |
|  | 2 | 122 |
|  | 1 | 117 |
|  | 0.5 | 108 |
| Doxorubicin | 8 | 185 |
|  | 4 | 141 |
|  | 2 | 126 |
|  | 1 | 122 |
|  | 0.5 | 106 |
| N-trifluoroacetyl-carminomycin | 25 | 123 |
|  | 12.5 | 104 |
|  | 6.25 | 106 |
|  | 3.1 | 106 |
|  | 1.56 | 98 |
| Carminomycin | 25 | 0 |
|  | 12.5 | 91 |
|  | 6.25 | 0 |
|  | 3.13 | 129 |
|  | 1.56 | 130 |

[a]Data obtained under auspices of National Cancer Institute.
[b]Median survival time expressed as percent of untreated controls.

The results of another series of experiments, under the same conditions as in Table 1, are reported in Table 2.

Table 2

|  | Dose mg./kg. | T/C[b] |
|---|---|---|
| Daunorubicin | 32 | 96 |
|  | 16 | 123 |
|  | 8 | 132 |
|  | 4 | 126 |
|  | 2 | 123 |
| Doxorubicin | 16 | 92 |
|  | 8 | 191 |
|  | 4 | 189 |
|  | 2 | 145 |
|  | 1 | 110 |
| N-trifluoroacetyl-carminomycin | 200 | 215 |
|  | 100 | 118 |
|  | 50 | 145 |
|  | 25 | 118 |
|  | 12.5 | 96 |

Variations and modifications can, of course, be made without departing from the spirit and scope of the invention.

Having thus described our invention, what we desire to secure by Letters Patent and hereby claim is:

1. An N-acyl derivative of carminomycin having the formula:

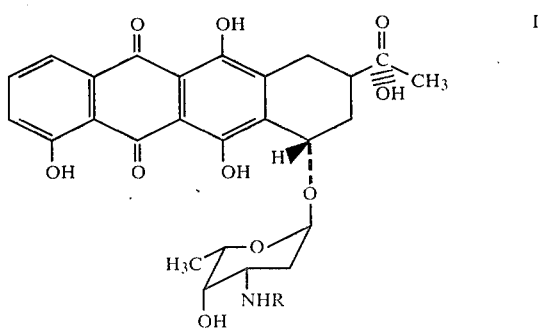

wherein R is an acyl group selected from the group consisting of acetyl, mono, di and trichloroacetyl, trifluoroacetyl and benzoyl.

2. An N-acyl derivative according to claim 1, wherein R is trifluoroacetyl.

3. A method of treating a host afflicted with transplanted $P_{388}$ lymphocytic leukemia which comprises intraperitoneally administering to a host afflicted with said tumor a therapeutically effective amount of an N-acyl derivative according to claim 1.

4. A method according to claim 3, wherein R is trifluoroacetyl.

* * * * *

UNITED STATES PATENT AND TRADEMARK OFFICE
CERTIFICATE OF CORRECTION

PATENT NO. : 4,188,377

DATED : Feb. 12, 1980

INVENTOR(S) : Antonino Suarato et al.

Page 1 of 2

It is certified that error appears in the above—identified patent and that said Letters Patent is hereby corrected as shown below:

Column 4, line 55:

"  " 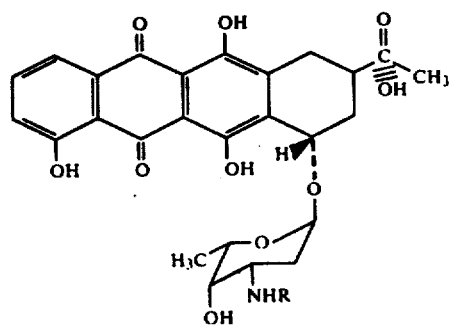  " should read

UNITED STATES PATENT AND TRADEMARK OFFICE
CERTIFICATE OF CORRECTION

PATENT NO. : 4,188,377

DATED : Feb. 12, 1980

INVENTOR(S) : Antonino Suarato et al.

It is certified that error appears in the above—identified patent and that said Letters Patent is hereby corrected as shown below:

-- 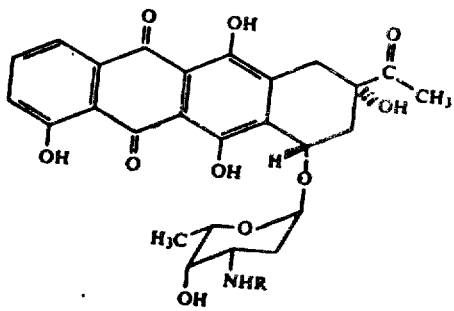 --.

Signed and Sealed this

Seventh Day of April 1981

[SEAL]

Attest:

RENE D. TEGTMEYER

Attesting Officer — Acting Commissioner of Patents and Trademarks